(12) United States Patent
Gordon et al.

(10) Patent No.: US 8,828,378 B2
(45) Date of Patent: *Sep. 9, 2014

(54) TARGETED VECTORS FOR CANCER IMMUNOTHERAPY

(75) Inventors: Erlinda M. Gordon, Glendale, CA (US); Frederick L. Hall, Glendale, CA (US)

(73) Assignee: The University of Southern California, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/724,317

(22) Filed: Mar. 15, 2010

(65) Prior Publication Data

US 2010/0233127 A1    Sep. 16, 2010

Related U.S. Application Data

(60) Continuation of application No. 11/483,017, filed on Jul. 7, 2006, now Pat. No. 7,708,986, which is a division of application No. 09/997,525, filed on Nov. 29, 2001, now abandoned.

(60) Provisional application No. 60/250,185, filed on Nov. 29, 2000.

(51) Int. Cl.
  *A01N 43/04*  (2006.01)
  *A61K 31/70*  (2006.01)
  *A61K 48/00*  (2006.01)
  *A01N 63/00*  (2006.01)

(52) U.S. Cl.
  USPC .................. 424/93.2; 514/44 R; 424/93.6

(58) Field of Classification Search
  USPC .................. 424/93.2, 93.6; 514/44 R
  See application file for complete search history.

(56) References Cited

U.S. PATENT DOCUMENTS

| | | |
|---|---|---|
| 5,328,470 A | 7/1994 | Nabel et al. |
| 5,354,674 A | 10/1994 | Hodgson |
| 5,512,421 A | 4/1996 | Burns et al. |
| 5,591,624 A | 1/1997 | Barber et al. |
| 5,643,770 A | 7/1997 | Mason et al. |
| 5,661,023 A | 8/1997 | Hrinda et al. |
| 5,670,488 A | 9/1997 | Gregory et al. |
| 5,710,022 A | 1/1998 | Zhu et al. |
| 5,800,811 A | 9/1998 | Hall et al. |
| 5,821,234 A | 10/1998 | Dzau |
| 5,952,225 A | 9/1999 | Pensiero et al. |
| 6,004,798 A | 12/1999 | Anderson et al. |
| 6,281,010 B1 | 8/2001 | Gao et al. |
| 6,818,439 B1 | 11/2004 | Jolly et al. |
| 7,060,811 B2 | 6/2006 | Aldaz et al. |
| 7,347,998 B2 | 3/2008 | Hall et al. |
| 8,052,966 B2 | 11/2011 | Hall et al. |
| 2002/0177571 A1 | 11/2002 | Gordon et al. |
| 2003/0027818 A1 | 2/2003 | Redmond et al. |
| 2004/0253215 A1 | 12/2004 | Hall et al. |
| 2006/0251627 A1 | 11/2006 | Gordon |
| 2007/0224188 A1 | 9/2007 | Allan et al. |
| 2007/0225603 A1 | 9/2007 | Jackson |
| 2008/0119572 A1 | 5/2008 | Owens et al. |
| 2009/0123428 A1 | 5/2009 | Hall et al. |

FOREIGN PATENT DOCUMENTS

| | | | |
|---|---|---|---|
| CA | 2595915 | 8/1998 | |
| EP | 0334301 B1 | 9/1998 | |
| WO | WO-95/25789 A1 | 9/1995 | |
| WO | WO 95/25789 A1 | 9/1995 | |
| WO | WO 96/30504 A1 | 10/1996 | |
| WO | WO 96/39430 A1 | 12/1996 | |
| WO | WO-98-01582 A1 | 1/1998 | |
| WO | WO 98/44938 | * 10/1998 | ............. A61K 38/00 |
| WO | WO 98/44938 A1 | 10/1998 | |
| WO | WO 98/51700 A1 | 11/1998 | |
| WO | WO 01/64870 A2 | 9/2001 | |
| WO | WO 01/64870 A3 | 1/2002 | |
| WO | WO-2004-044394 | 6/2002 | |

OTHER PUBLICATIONS

2004, Ghezzi et al., Cell Death and Differentiation, vol. 11, pp. S37-S44.*
2002, Geddis et al., Cytokine and Growth Factor Rev., vol. 13, pp. 61-73.*
1999, Huang et al., Nature Cell Biology, vol. 1, pp. E131-E138.*
2005, Arnold et al., Cancer, vol. 104, pp. 2035-2047.*
2004, Lowenfels et al., Jpn. J. Clin. Oncol., vol. 34(5), pp. 238-244.*
Liberman et al., 2003, Breast Cancer Res. and Treatment, vol. 80, pp. 115-126.*
Principles of Anatomy and Physiology, 2006, Wiley, 11th Ed., pp. 99-100 and 689-690.*
Gordon et al., Int. J. Oncolocy, 2007, vol. 30, pp. 1297-1307.*
Gordon et al., Int. J. Oncolocy, 2006, vol. 29, pp. 1053-1064.*
Reference #2.*
Reference #3.*
Reference #4.*
Reference #5.*
Reference #6.*
Reference #8.*
Palu et al., 1999, Gene Therapy, vol. 6, pp. 330-337.*
Benedetti et al. Human Gene Therapy, vol. 8, pp. 1345-1353, 1997.*
Fields-Berry et al. (1992, PNAS, vol. 89, pp. 693-697).*
Lenz et al., "Tumor site-specific phase I/II evaluation of the safety and efficacy of hepatic arterial infusion of a matrix-targeted retroviral vector bearing a dominant negative cyclin G1 (dnG1) construct as treatment for colorectal carcinoma metastatic to liver," Human Gene Therapy 12:1563-1565 (2001).

(Continued)

*Primary Examiner* — Anoop Singh
*Assistant Examiner* — David A Montanari
(74) *Attorney, Agent, or Firm* — Wilson, Sonsini, Goodrich & Rosati

(57) ABSTRACT

This invention provides compositions and methods for treating cancer. More specifically this invention is directed to a targeted retroviral vector comprising a cytokine gene that can be administered either alone or in combination with a targeted retroviral vector comprising a cytocidal gene for treating cancer in a subject. Also provided are a kit or drug delivery system comprising the compositions for use in the methods described.

6 Claims, 6 Drawing Sheets

(56) References Cited

OTHER PUBLICATIONS

Figure 1:
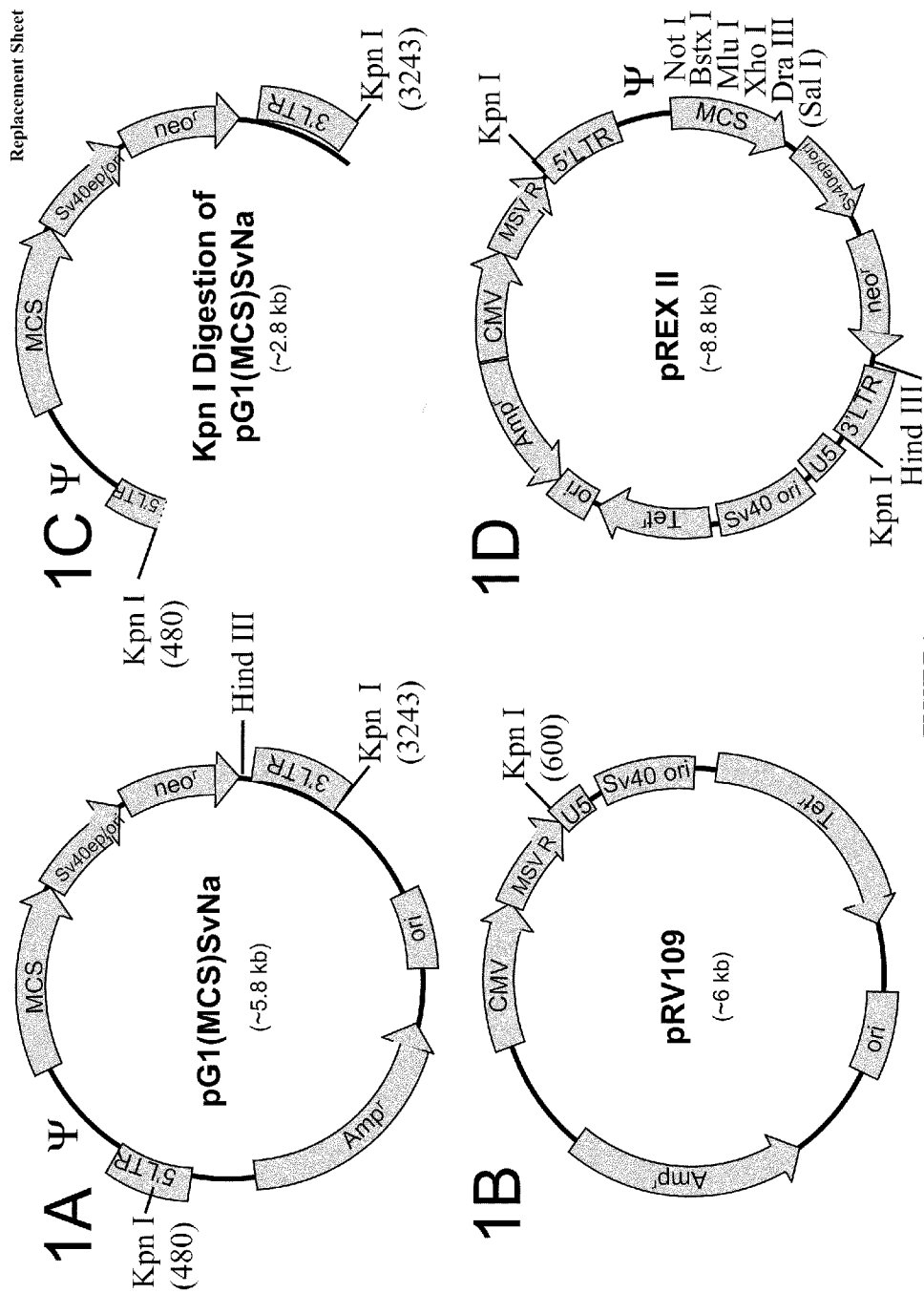
Figure 1:
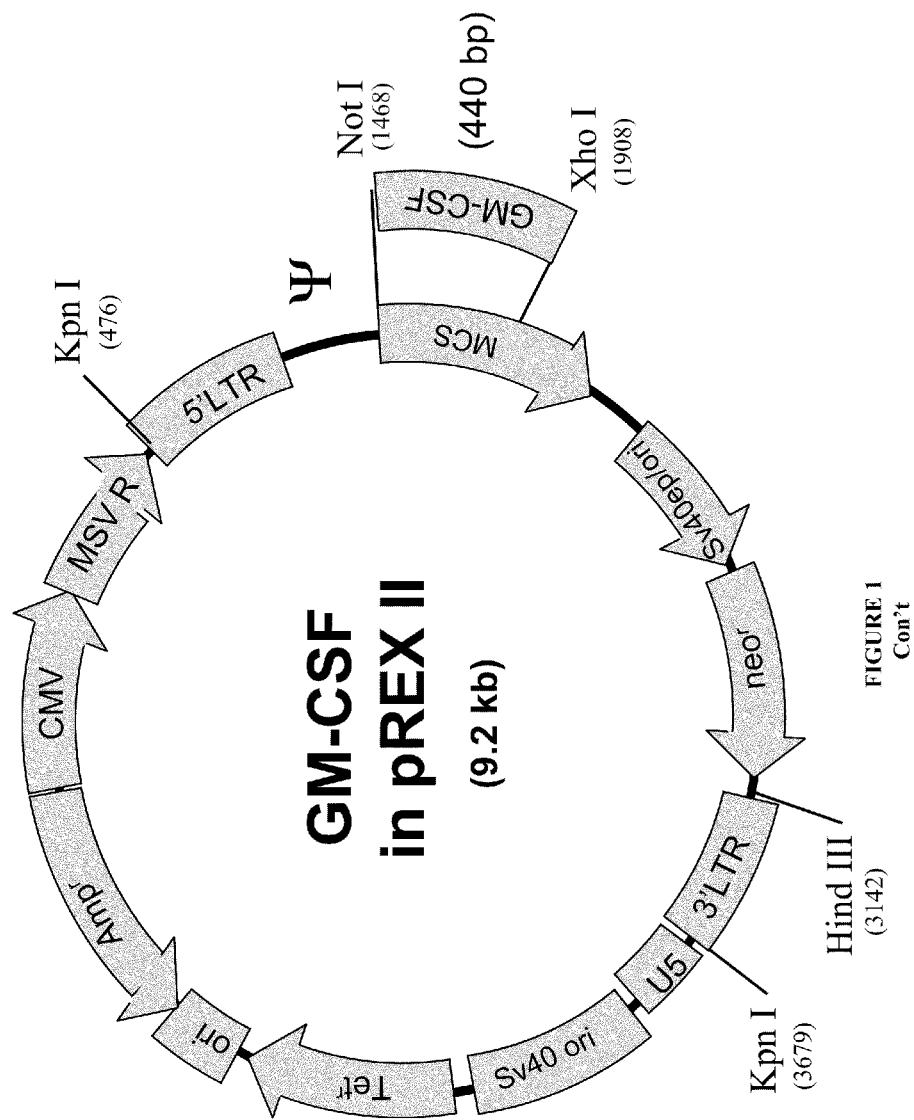

Nagano et al., "Gene therapy eradicating distant disseminated micrometastases by optimal cytokine expression in the primary lesion only: novel concepts for successful cytokine gene therapy," Intl J Onc 24:549-558 (2004).
U.S. Appl. No. 10/829,926 Office Action mailed Aug. 9, 2010.
U.S. Appl. No. 12/235,592 Office Action mailed Aug. 19, 2010.
Shidong, et al. "Dosimetric and Technical Considerations for Interstitial Adenoviral Gene Therapy as Applied to Prostate Cancer" Int. Journal Radiation Oncology Biol. Phys. 55(1):204-214 (2003).
Supplementary European Search Report dated Feb. 22, 2011 for PCT Application No. US07/023305.
U.S. Appl. No. 10/829,926 Office Action mailed Feb. 28, 2011.
Anderson, W. Human Gene Therapy. Nature. 1998; 392:25-30.
Arap, et al. Cancer Treatment By Targeted Drug Delivery to Tumor Vasculature In A Mouse Model. Science. 1998; 279:377-380.
Asher et al. Murine Tumor Cells Transduced with the Gene for Tumor Necrosis Factor-α The Journal of Immunology. 1991; 146:3227-3234.
Behrens, et al. Retroviral gene therapy vectors for prevention of excimer laser-induced corneal haze. Invest Ophthalmol Vis Sci. 2002;43(4):968-77.
Blankenstein, et al. Tumor Suppression after Tumor Cell-targeted Tumor Necrosis Factor α Gene Transfer. The Journal of Experimental Medicine. 1991; 173:1047-1052.
Borrello, et al. A Universal Granulocyte-Macrophage Colony-Stimulating Factor-Producing Bystander Cell Line for Use in the Formulation of Autologous Tumor Cell-Based Vaccines. Human Gene Therapy. 1999; 10:1983-1991.
Cosset, et al. Retroviral Retargeting by Envelopes Expressing an N-Terminal binding domain. J Virol. 1995; 69:6314-6322.
Cosset, et al. Targeting Retrovirus Entry. Gene Therapy. 1996; 3:946-956.
Coze, et al. Characteristics and Immunomodulatory Properties of Human Neuroblastoma Cells after Retrovirus-Mediated Gene Transfer of the Cytokine Genes IL-2 and IFN-(. Transgenics. 1995; 1:585-595.
Dang, et al. Gene therapy and translational cancer research. Clin. Cancer Res. 1999; 5:471-474.
Dranoff, et al. Vaccination with irradiated tumor cells engineered to secrete murine granulocyte-macrophage colony-stimulating factor stimulates potent, specific, and long-lasting anti-tumor immunity. Proceedings of the National Academy of Sciences. 1993; 90:3539-3543.
El Kamar, et al. Metastatic Pancreatic Cancer: Emerging Strategies in Chemotherapy and Palliative Care. The Oncologist. 2003; 8:18-34.
Fearon, et al. Interleukin-2 Production by Tumor Cells Bypasses T Helper Function in the Generation of an Antitumor Response. Cell. 1990; 60:397-403.
Fong, et al. The Use and Development of Retroviral Vectors to Deliver Cytokine Genes for Cancer Therapy. Critical Reviews in Therapeutic Drug Carrier Systems. 2000; 17:1-60.
Foreman, et al. Mechanisms of selective killing of neurobalstoma cells by natural killer cells and lymphokine activated killer cells. Potential for residual disease eradication. British Journal of Cancer. 1993; 67:933-938.
Gansbacher, et al. Retroviral lymphokine gene transfer induced secretion of Interleukin-2 (IL-2) or Interferon-gamma (IFN-() by human melanoma cells. Eighty-Second annual meeting of the American Association for Cancer Research Proceedings, Houston, Texas. 1991;32:1514.
Gardlik, et al. Vectors and delivery systems in gene therapy. Med. Sci. Monit. 2005; 11:RA110-121.
Gilboa. Immunotherapy of Cancer with Genetically Modified Tumor Vaccines. Seminars in Oncology. 1996; 23:101-107.
Golumbek. Treatment of Established Renal Cancer by Tumor Cells Engineered to Secrete Interleukin-4. Sciences. 1991; 254:713-716.
Goncalves, M. A concise peer into the background, initial thoughts and practices of human gene therapy. BioEssays. 2005; 27:506-517.

Gordon, et al. Capture and expansion of bone marrow-derived mesenchymal progenitor cells with a transforming growth factor-β1-von Willebrand's factor fusion protein for retrovirus-mediated delivery of coagulation factor IX. Human Gene Therapy. 1997; 8:1385-1394 (Abstract).
Gordon, et al. First clinical experience using a 'pathotropic' injectable retroviral vector (Rexin-G) as intervention for stage IV pancreatic cancer. Int J Oncol. 2004;24(1):177-85.
Gordon, et al. Genetic Engineering of Targeted Retroviral Vectors. Vector Targeting Strategies for Therapeutic Gene Delivery. 2002; 293-320.
Gordon, et al. Inhibition of Metastatic Tumor Growth in Nude Mice by Portal Vein Infusions of Matrix-targeted Retroviral Vectors Bearing a Cytocidal Cyclin G1 Construct. Cancern Research. 2000; 60:3343-3347.
Gordon, et al. Le morte du tumour: histological features of tumor destruction in chemo-resistant cancers following intravenous infusions of pathotropic nanoparticles bearing therapeutic genes. Int J Oncol, 2007; 30(6):1297-307.
Gordon, et al. Lesion-targeted injectable vectors for vascular restenosis. Hum Gene Ther. 2001;12(10):1277-87.
Gordon, et al. Pathotropic nanoparticles for cancer gene therapy Rexin-G IV: three-year clinical experience. Int J Oncol. 2006; 29(5):1053-64.
Gordon, et al. Systemic Administration of a Matrix-Targeted Retroviral Vector is Efficacious for Cancer Gene Therapy in Mice. Human Gene Therapy. 2001; 12:193-204.
Guinan, et al. Pivotal Role of the B7:CD28 Pathway in Transplantation Tolerance and Tumor Immunity. Blood. 1994; 84:3261-3282.
Hall, et al. Molecular Engineering of Matrix-Targeted Retroviral Incorporating a Surveillance Function Inherent in von Willebrand Factor. Human Gene Therapy. 2000; 11:983-993.
Hall, et al. Targeting Retroviral Vectors to Vascular Lesions by Genetic Engineering of the MoMuIV gp70 Envelope Protein. Human Gene Therapy. 1997; 8:2183-2192.
Handgretinger, et al. Interferon-Gamma Upregulates the Susceptibility of Human Neuroblastoma Cells to Interleukin-2-Activated Natural Killer Cells. Natural Immunity and Cell Growth Regulation. 1989; 8:189-196.
Hock, et al. Interleukin 7 Induces $CD4^+T$ Cell-dependent Tumor Rejection. The Journal of Experimental Medicine. 1991; 174:1291-1298.
Hu, et al. Design of Retroviral Vectors and Helper Cells for Gene Therapy. Pharmacology Reviews. 2000; 52:493-511.
Jaffee. Immunotherapy of Cancer. Annals of The New York Academy of Sciences. 886:67-72.
Kasahara, et al. Tissue-Specific Targeting of Retroviral Vectors Through Ligand-Receptor interactions. Science. 1994; 266:1373-1376.
Kay, et al. Evidence for gene transfer and expression of factor IX in Hemophillia B Patients. Nature Genetics. 2000; 24:257-261.
Kim, et al. Macrophage Colony-Stimulating Factor Can Modulate Immune Responses and Attract Dendritic Cells in Vivo. Human Gene Therapy. 2000; 11:305-321.
Klagsbrun, et al. Regulators of Angiogenesis. Annual Review of Physiology. 1991; 53:217-239.
Knobloch, et al. T cell receptor diversity in severe combined immunodeficiency following HLA-haploidentical bone marrow transplantation. Bone Marrow Transplantation. 1991; 8:383-387.
Kotani et al. Improved Methods of Retroviral Vector Transduction and production for Gene Therapy. Human Gene Therapy. 1994; 5:19-28.
Kurane, et al. Cytokines as an Adjuvant to Tumor Vaccines: Efficacy of Local Methods of Delivery. Annals of Surgical Oncology. 1997; 4:579-585.
Kuvshinoff, et al. Treatment of Respectable and Locally Advanced Pancreatic Cancer. Cancer Control. 2000; 7:428-436.
Lenz et al. Tumor Site-Specific Phase I Evaluation of Safety of Hepatic Arterial Infusion of a matrix-Targeted Retroviral Vector Bearing a Dominant Negative Cyclin G1 Construct as Intervention for Colorectal Carcinoma Metastatic to the Liver. Human Gene Therapy. 2002; 13:1515-1537.

(56) References Cited

OTHER PUBLICATIONS

Lieberman, et al. Innovative Treatments for Pancreatic Cancer. Surg Clin North Am. 2001; 81:715-739.
Liu, et al. Incorporation of Tumor Vasculature Targeting Motifs into Moloney Murine Leukemia Virus Env Escort Proteins Enhances Retrovirus Binding and Transduction of Human Endothelial Cells. Journal of Virology. 2000; 74:5320-5328.
Mackensen, et al. Immunostimulatory Cytokines in Somatic Cells and Gene Therapy of Cancer. Cytokine and Growth Factor Reviews. 1997; 8:119-128.
Magovern, et al. Regional Angiogenesis Induced in Nonischemic Tissue by an Adenoviral Vector Expressing Vascular Endothelial Growth Factor. Human Gene Therapy. 1997; 8:215-227.
Main, et al. Human Neuroblastoma Cell Lines are Susceptible to Lysis by Natural Killer Cells But Not by Cytotoxic T Lymphocytes. The Journal of Immunology. 1985; 135:242-246.
Marin, et al. Targeted Infection of Human Cells Via Major Histocompatibility Complex Class 1 Molecules by Moloney Murine Leukemia Virus-Derived Viruses Displaying Single-Chain Antibody Fragment-Envelope Fusion Proteins. Journal of Virology. 1996; 70:2957-2962.
Martin, et al. Retroviral Vector Targeting to Melanoma Cells by Single-Chain Antibody Incorporation in Envelope. Human Gene Therapy. 1998; 9:737-746.
Masood, et al. Retroviral Vectors Bearing IgG-binding Motifs for Antibody-Mediated Targeting of Vascular Endothelial Growth Factor Receptors. Int'l J Mol Med. 2001; 8:335-343.
Mellstedt, et al. Augmentation of the Immune response with granulocyte-macrophage colony-stimulating factor and other hematopoietic growth factors. Current Opinion in Hematology. 1999; 6:169-175.
Mendiratta, et al. Combination of Interleukin 12 and interferon α Gene therapy Induces a Synergistic Antitumor Response against Colon and Renal Cell Carcinoma. Human Gene Therapy. 2000: 11:1851-1862.
Miller, et al. Improved Retroviral Vectors for Gene Transfer and Expression. Biotechniques. 1989; 7:984-990.
Miller, et al. Intratumoral Administration of Adenoviral Interleukin 7 Gene-Modified Dendritic Cells Augments Specific Antitumor Immunity and Achieves Tumor Eradication. Human Gene Therapy. 2000; 11:53-65.
Morgan, et al. Analysis of the Functional and Host Range-Determining Regions of the Murine Ecotropic and Amphotropic Retrovirus Envelope Proteins. Journal of Virology. 1993; 67:4712-4721.
Nabel, et al. Direct gene transfer with DNA-liposome complexes in melanoma: Expression, biologic activity, and lack of toxicity in humans. Proceedings of the National Academy of Sciences. 1993; 90:11307-11311.
Nagai, et al. Irradiated tumor cells adenovirally engineered to secrete granculocyte/macrophage-colony-stimulating factor establish anti-tumor immunity and eliminate pre-existing tumors in syngeneic mice. Cancer Immunology Immunotherapy. 1998; 47:72-80.
Neda, et al. Chemical Modification of an Ecotropic Murine Leukemia Virus Results in Redirection of Its Target Cell Specificity. The Journal of Biological Chemistry. 1991; 266:14143-14146.
Nishi, et al. Collagen-binding growth factors: Production and characterization of functional fusion proteins having a collagen-binding domain. Proc. Natl. Acad. Sci. USA. 1998; 95:7018-7023.
Ohno, et al. Cell-Specific Targeting of Sindbis Virus Vectors Displaying IgG-binding domains of Protein. A. Nat Biotechnol. 1997; 15:763-767.
O'Reilly, et al. Endostatin: An Endogenous Inhibitor of Angiogenesis and Tumor Growth. Cell. 1997; 88:277-285.
Peng, et al. Viral Vector Targeting. Curr Opin Biotechnol. 1999; 454-457.
Romano, et al. Latest developments in gene transfer technology. Achievements, perspectives, and controversies over therapeutic applications. Stem Cells. 2000; 18:19-39.
Rosemurgy, et al. New Directions in Systemic Therapy of Pancreatic Cancer. Cancer Control. 2000; 7:437-444.
Rosenberg, et al. Gene Transfer into Human-Immunotherapy of Patients With Advanced Melanoma, Using Tumor Infiltrating Lymphocytes Modified by Retroviral Gene Transduction. New England Journal of Medicine. 1990; 323:570-578.
Rosenberg, et al. Immunization of Cancer Patients Using Autologous Cancer Cells Modified by Insertion of the Gene for InterLeukin2. Human Gene Therapy. 1992; 3:75-90.
Russell, et al. Retroviral Vectors Displaying Functional Antibody Fragments. Nucl Acid Res. 1993; 21:1081-1085.
Sadler, et al. Cloning and characterization of two cDNAs coding for human von Willebrand factor. Natl. Acad. Sci. USA. 1985; 82:6394-6398.
Skotzko, et al. Retroviral Vector-mediated Gene Transfer of Antisense Cyclin G1 (CYCG1) Inhibits Proliferation of Human Osteogenic Sarcoma Cells. Cancer Research. 1995; 55:5493-5498.
Somia, et al. Generation of Targeted Retroviral Vectors by Using Single-Chain Variable Fragment: An Approach to In Vivo Gene Delivery. Proc Natl Acad Sci USA. 1995; 92:7570-7574.
Soneoka, et al. A transient three-plasmid expression system for the production of high titer retroviral vectors. Nucleic Acids Research. 1995; 23:628-633.
Song, et al. Phase I/II evaluation of safety and efficacy of a matrix-targeted retroviral vector bearing a dominant negative cyclin G1 construct (Md-dnG1) as adjunctive intervention for superficial corneal opacity/corneal scarring. Hum Gene Ther. 2003;14(3):306-9.
Stromblad, et al. Cell Adhesion and Angiogenesis. Trends Cell, Biol. 1996; 64:462-467.
Suh, et al. Treatment of Liver Metastases from Colon Carcinoma with Autologous Tumor Vaccine Expressing Granulocyte-Macrophage Colony-stimulating Factor. Journal of Surgical Oncology. 1999; 72:218-224.
Takagi, et al. A Collagen/Gelatin-Binding Decapeptide Derived from Bovine Propolypeptide of von Willebrand Factor. Biochemistry. 1992; 31:8530-8534.
Takagi, et al. Collagen-Binding Domain Within Bovine Propolypeptide of Von Willebrand Factor. J. Biol Chem. 1991; 266:5575-5579.
Tepper, et al. Experimental and Clinical Studies of Cytokine Gene-Modified Tumor Cells. Human Gene Therapy. 1994; 5:153-164.
Tseng, et al. Gene Therapy for Pancreatic Cancer. Surg Oncol Clin N. Am. 2002; 11:537-569.
Ucar, et al. Sustained cytokine production and immunophenotypic changes in human neuroblastoma cell lines transduced with a human gamma interferon vector. Cancer Gene Therapy. 1995; 2:171-181.
Valsesia-Wittman, et al. Modification in the Binding Domain of Avian Retrovirus Envelope Protein to Redirect the Host Range of Retroviral Vectors. Journal of Virology. 1994; 68:4609-4619.
Van Riel, et al. Pancreaticobiliary Cancer: The Future Aspects of Medical Oncology. Ann Oncol. 1999; 10:296-299.
Verma, et al. Gene Therapy-Promises, Problems and Prospects. Nature. 1997; 389:239-242.
Verma, et al. Gene Therapy: Twenty-first century medicine. Annu. Rev. Biochem. 2005; 74:711-738.
Warren, et al. Uses of granulocyte-macrophage colony-stimulating factor in vaccine development. Current Opinion in Hematology. 2000, 7:168-173.
Watanabe, et al. Exogenous expression of mouse interferon γ cDNA in mouse neuroblastome C1300 cells results in reduced tumorigenicity by augmented anti-tumor immunity. Proceedings of the National Academy of Sciences. 1989; 86:9456-9459.
Wu, et al. Characterization of the Proline-Rich Region of Murine Leukemia Virus Envelope Protein. Journal of Virology. 1998; 72:5383-5391.
Wu, et al. Molecular Cloning of the Human CYCG1 Gene Encoding a G-Type Cyclin: Overexpression in Human Osteosarcoma Cells. Oncology Reports. 1994; 1:705-711.
Xie, et al. Elements within the First 17 Amino Acids of Human Osteonectin Are Responsible for Binding to Type V Collagen. The Journal of Biological Chemistry. 1996; 271:8121-8125.

(56) References Cited

OTHER PUBLICATIONS

Xu et al. Long Term Inhibition of Neointima Formation in Balloon-Injured Rat Arteriesby Intraluminal Instillation of a Matrix-Targeted Retroviral Vector Bearing an Improved Cytocidal Cyclin G1 Construct. Intl J Mol Med. 2001; 8:19-30.
Yang, et al. Development of Novel Cell Surface CD34-Targeted Recombinant Adenoassociated Virus Vector for Gene Therapy. Human Gene Therapy. 1998; 9:1929-1937.
Yang, et al. Generation of Retroviral Vector for Clinical Studies using Transient Transfection. Human Gene Therapy. 1999; 10:123-132.
Zhao, et al. Identification of the Block in Targeted Retroviral-Mediated Gene Transfer. Proc National Academy of Science USA. 1999; 96:4005-4010.
Zwiebel, J. Cancer Gene and Oncolytic Virus Therapy. Semin Oncol. 2001; 28:336-343.
Baum et al., "Side effects of retroviral gene transfer into hematopoietic stem cells," Blood 101:2099-2114 (2003).
Hacien-Bey-Abina et al., "LMO2-Associated Clonal T Cell Proliferation in Two Patients after Gene Therapy for SCID-X1," Science 302:415-419 (2003).
Kustikova et al., "Dose finding with retroviral vectors: correlation of retroviral vector copy numbers in single cells with gene transfer efficiency in a cell population," Blood 102:3934-3937 (2003).
Diehl et al., "A Dominant-Negative Cyclin D1 Mutant Prevents Nuclear Import of Cyclin-Dependent Kinase 4 (CDK4) and Its Phosphorylation by CDK-Activating Kinase," Mol. Cell Biol. 17(12):7362-7374 (1997).
Geddis et al., "Thrombopoietin: a pan-hematopoietic cytokine," Cytokine & Growth Factor Reviews 13:61-67 (2002).
Ghezzi et al., "Erythropoietin as an antiapoptotic, tissue-protective cytokine," Cell Death & Differentiation 11:537-544 (2004).
Hinds et al., "Function of a human cyclin gene as an oncogene," PNAS USA 91:709-713 (1994).
Addison et al., "Comparison of the human versus murine cytomegalovirus immediate early gene promoters for transgene expression by adenoviral vectors," J. Gen. Virol. 78:1653-1661 (1997).
Chen et al., "Combination suicide and cytokine gene therapy for hepatic metastases of colon carcinoma: Sustained antitumor immunity prolongs animal survival," Cancer Res. 46:3758-3762 (1996).
Kafri et al., "Sustained expression of genes delivered directly into liver and muscle by lentiviral vectors," Nature Genetics 17:314-317 (1997).
Rousculp et al., "Quantitative evaluation of retroviral gene transduction efficiency in human lung cancer cells," Human Gene Therapy 3:471-477 (1992).
U.S. Appl. No. 11/556,666 Office Action dated Jan. 12, 2010 Advisory Action.
U.S. Appl. No. 11/556,666 Office Action dated Oct. 13, 2009.
U.S. Appl. No. 11/556,666 Office Action dated Dec. 24, 2008.
U.S. Appl. No. 11/483,017 Office Action dated Aug. 14, 2009.
U.S. Appl. No. 11/483,017 Office Action dated Mar. 5, 2009.
U.S. Appl. No. 11/483,017 Office Action dated Jun. 20, 2008.
U.S. Appl. No. 11/483,017 Office Action dated Dec. 13, 2007.
U.S. Appl. No. 09/997,525 Office Action dated Feb. 3, 2006.
U.S. Appl. No. 09/997,525 Office Action dated Jul. 28, 2005.
U.S. Appl. No. 09/997,525 Office Action dated Dec. 18, 2004.
U.S. Appl. No. 09/997,525 Advisory Action dated Sep. 13, 2004.
U.S. Appl. No. 09/997,525 Office Action dated May 18, 2004.
U.S. Appl. No. 09/997,525 Office Action dated Aug. 21, 2003.
U.S. Appl. No. 12/235,592 Office Action dated Jan. 28, 2010.
Langreth et al., "Researchers get dose of reality as logistics stymie gene therapy," The Wall Street Journal, Oct. 27, 1999 (5 pages).
James et al., "Measuring response in solid tumors: Unidimensional versus bidimensional measurement," J. Natl. Cancer Inst. 91:523-528 (1999).
Hall et al., "Design, expression, and renaturation of a lesion-targeted recombinant epidermal growth factor-von Willebrand factor fusion protein: efficacy in an animal model of experimental colitis," Int. J. Mol. Med. 6(6):635-643 (2000).

Blackwell, et al. Retargeting to EGFR enhances adenovirus infection efficiency of squamous cell carcinoma. Arch Otolaryngol Head Neck Surg. Aug. 1999;125(8):856-63.
Chu, et al. Toward highly efficient cell-type-specific gene transfer with retroviral vectors displaying single-chain antibodies. J Virol. Jan. 1997;71(1):720-5.
Drapkin, et al. Targeting the urokinase plasminogen activator receptor enhances gene transfer to human airway epithelia. J Clin Invest. Mar. 2000;105(5):589-96.
European search report dated Oct. 31, 2007 for Application No. 04760083.8.
Goldman, et al. Targeted gene delivery to Kaposi's sarcoma cells via the fibroblast growth factor receptor. Cancer Res. Apr. 15, 1997;57(8):1447-51.
Han, et al. Ligand-directed retroviral targeting of human breast cancer cells. Proc Natl Acad Sci U S A. Oct. 10, 1995;92(21):9747-51.
International search report dated Oct. 6, 2008 for PCT Application No. US07/23305.
International search report dated Jul. 21, 2005 for PCT Application No. US04/012302.
Kasono, et al. Selective gene delivery to head and neck cancer cells via an integrin targeted adenoviral vector. Clin Cancer Res. Sep. 1999;5(9):2571-9.
McDonald, et al. Efficient adenoviral gene transfer to kidney cortical vasculature utilizing a fiber modified vector. J Gene Med. Mar.-Apr. 1999;1(2):103-10. (Abstract only).
Nicklin, et al. Selective targeting of gene transfer to vascular endothelial cells by use of peptides isolated by phage display. Circulation. Jul. 11, 2000;102(2):231-7.
Ohno, et al. Retrovirus vectors displaying the IgG-binding domain of protein A. Biochem Mol Med. Oct. 1997;62(1):123-7.
Printz, et al. Fibroblast growth factor 2-retargeted adenoviral vectors exhibit a modified biolocalization pattern and display reduced toxicity relative to native adenoviral vectors. Hum Gene Ther. Jan. 1, 2000;11(1):191-204. (Abstract only).
Rancourt, et al. Basic fibroblast growth factor enhancement of adenovirus-mediated delivery of the herpes simplex virus thymidine kinase gene results in augmented therapeutic benefit in a murine model of ovarian cancer. Clin Cancer Res. Oct. 1998;4(10):2455-61.
Reynolds, et al. A targetable, injectable adenoviral vector for selective gene delivery to pulmonary endothelium in vivo. Mol Ther. Dec. 2000;2(6):562-78.
Romanczuk, et al. Modification of an adenoviral vector with biologically selected peptides: a novel strategy for gene delivery to cells of choice. Hum Gene Ther. Nov. 1, 1999;10(16):2615-26. (Abstract only).
Therasse, et al. New guidelines to evaluate the response to treatment in solid tumors. J Natl Cancer Inst. Feb. 2, 2000;92(3):205-16.
Van Beusechem, et al. Efficient and selective gene transfer into primary human brain tumors by using single-chain antibody-targeted adenoviral vectors with native tropism abolished. J Virol. Mar. 2002;76(6):2753-62.
Vanderkwaak, et al. An advanced generation of adenoviral vectors selectively enhances gene transfer for ovarian cancer gene therapy approaches. Gynecol Oncol. Aug. 1999;74(2):227-34. (Abstract only).
Wickham, et al. Targeting endothelium for gene therapy via receptors up-regulated during angiogenesis and inflammation. Cancer Immunol Immunother. Nov.-Dec. 1997;45(3-4):149-51. (Abstract only).
Pan and Whitley, "Closed hollow-fiber bioreactor: a new approach to retroviral vector production," J. Gene Med. 1(6):433-440 (1999).
Reeves and Cornetta, "Clinical retroviral vector production: step filtration using clinically approved filters improves titers," Gene Therapy 7:1993-1998 (2000).
Gordon et al. Inhibition of Metastatic Tumor Growth in Nude Mice by Portal Vein Infusions of Matrix-targeted Retroviral Vectors Bearing a Cytocidal Cyclin G1 Construct. Cancern Research. 2000; 60:3343-3347.

(56) References Cited

OTHER PUBLICATIONS

Jones et al. Antibodies for targeted gene therapy: extracellular gene targeting and intracellular expression. Advanced Drug Delivery Reviews. 1998; 31:153-170.

Marjmdar et al. "Efficacy of herpes simplex virus thymidine kinase in combination with cytokine gene therapy in an experimental metastatic breasat cancer model." Cancer Gene Ther., 2000, 7(7):1086-99.

Williams et al. Identification of a novel cyclin-like protein in human tumor cells. Journal of Biological Chemistry. 1993; 268:8871-8880.

\* cited by examiner

Con't

TARGETED VECTORS FOR CANCER IMMUNOTHERAPY

1. RELATED APPLICATIONS

This application is a continuation application of U.S. application Ser. No. 11/483,017, now U.S. Pat. No. 7,708,986, filed Jul. 7, 2006, which is a divisional application of U.S. application Ser. No. 09/997,525, filed Nov. 29, 2001, now abandoned, which claims the benefit under 35 U.S.C. 119(e) of provisional application Ser. No. 60/250,185 filed Nov. 29, 2000. The entire disclosure of each of these priority applications is hereby incorporated by reference.

2. FIELD OF THE INVENTION

This invention is in the field of oncology, more specifically this invention relates to targeted injectable vectors, such as targeted retroviral particles, for use in cancer to immunotherapy.

3. BACKGROUND OF THE INVENTION

Immune modulation in conjunction with tumor antigen presentation is a promising approach for optimizing the efficacy of cancer gene therapy protocols for metastatic cancer or minimal residual disease. In tumor vaccine strategies, cytokines such as granulocyte-macrophage colony-stimulating factor (GM-CSF) are employed to recruit antigen-presenting cells, including dendritic cells and macrophages, which result in the activation of cytotoxic T lymphocytes (CTL) against proteins expressed by cancer cells (Warren and Weiner, 2000; Kim et al., 2000). GM-CSF induces activation, proliferation, and differentiation of a variety of immunologically active cell populations, thereby facilitating the development of both humoral and cellular-mediated immunity (Warren and Weiner, 2000). One promising vaccine approach involves the insertion of the GM-CSF gene into autologous cancer cells that are then used for immunization (Jaffee, 1999; Suh et al., 1999). These genetically engineered tumor cells produce the GM-CSF protein in the local environment of tumor cells, thereby activating the patients T cells, which then function to eradicate the cancer at metastatic sites. Whether delivered as genetically engineered tumor cells or as the soluble GM-CSF protein, the cytokine must be present in the same site as the vaccine component (Mellstedt et al., 1999). Indeed, the establishment of specific and long lasting antitumor immunity following vaccination with GM-CSF tumor cells requires the simultaneous presence of GM-CSF and tumor antigens at the vaccination site (Nagai et el., 1998). However, in spite of the therapeutic potential demonstrated in animal models and early-phase clinical trials, the clinical development of these protocols has been limited by difficulties relating to the establishment of autologous tumor cell cultures (Fong et al., 2000) and the performance of individualized gene transfer procedures ex vivo (Borrello et al., 1999). Alternatively, local delivery of GM-CSF by direct intratumoral injection, as well as paracrine secretion by genetically engineered cells, has been shown to be more effective in upregulating lymph node sensitization when compared to systemic administration (Kurane et al., 1997).

A novel cancer immunotherapy approach for metastatic cancer would exploit the potential of systemically administered matrix-targeted retroviral vectors, infused sequentially intravenously, to efficiently deliver both a cytokine gene and/or a cytocidal construct to tumor cells and associated tumor vasculature. The efficacy of matrix-targeted gene delivery has been demonstrated in models of liver metastasis (Gordon et al., 2000a) and subcutaneous human cancer xenografts in nude mice (Gordon et al., 2000b). The present invention provides targeted retroviral paticles, for systemic administration, carrying one or more cytokine genes that provide high level efficiency of cytokine gene delivery into a tumor and recruitment of host mononuclear cells (tumor infiltrating lymphocytes) into the tumor.

4. SUMMARY OF THE INVENTION

This invention relates in general to compositions and methods for use in cancer immunotherapy. More particularly this invention is directed to targeted injectable vectors for use in cancer immunotherapy.

It is an object of this invention to provide a targeted retroviral particle comprising a modified viral surface protein for targeting the vector and a cytokine gene.

It is an object of this invention to provide a targeted retroviral particle comprising a modified viral surface protein for targeting the vector to an extracellular matrix component or tumor vasculature and a cytokine gene.

It is a further object of this invention to provide a targeted retroviral particle comprising a modified viral surface protein for targeting the vector particle to an extracellular matrix component comprising a binding region which binds to an extracellular matrix component and a cytokine gene (e.g., granulocyte-macrophage colony-stimulating factor (GM-CSF)).

It yet another object of this invention to provide a targeted retroviral particle comprising a modified viral surface protein for targeting the vector particle (e.g., targeting an extracellular matrix component or tumor vasculature) and a cytokine gene (e.g., GM-CSF) and a targeted retroviral particle comprising a modified viral surface protein for targeting the vector particle (e.g., targeting an extracellular matrix component or tumor vasculature) and a cytocidal gene (e.g., tumor suppressor genes).

It is another object of this invention to provide a targeted retroviral particle comprising a modified viral surface protein for targeting the vector (e.g., targeting an extracellular matrix component or tumor vasculature) and a cytokine gene (e.g., GM-CSF) and/or a targeted retroviral particle comprising a modified viral surface protein for targeting the vector particle (e.g., targeting an extracellular matrix component or tumor vasculature) and a cytocidal gene (e.g., tumor suppressor genes) to be administered intravenously or intra-arterially.

Yet another object of this invention is a method of treating cancer in a subject comprising administering a targeted retroviral particle comprising a modified viral surface protein for targeting the vector and a cytokine gene either alone or in conjunction with a targeted retroviral particle comprising a modified viral surface protein for targeting the vector particle and a cytocidal gene.

It is a further object of this invention to provide a method of treating primary tumors or tumors located in surgically inaccessible sites in a subject comprising administering a targeted retroviral particle comprising a modified viral surface protein for targeting the vector and a cytokine gene either alone or in conjunction with a targeted retroviral particle comprising a modified viral surface protein for targeting the vector particle and a cytocidal gene.

It is yet another object of this invention to provide methods of administering targeted injectable vectors, such as targeted retroviral particles to achieve high level efficiency of cytokine gene delivery into distant tumor sites resulting in secretion of GM-CSF by transduced tumor cells within the solid tumor and/or recruitment of host immune cells (e.g., mononuclear cells), such as tumor infiltrating lymphocytes (TIL) into the tumor.

It is a further object of this invention to provide a kit or drug delivery system comprising the compositions for use in the methods described herein.

5. BRIEF DESCRIPTION OF FIGURES

FIG. 1 shows a schematic diagram of the molecular engineering of the GM-CSF retroviral expression vector. The retroviral expression vector (pREX II) was created by engineering a multiple cloning site (MSC) into the G1XSvNa vector (Genetic Therapy, Inc.) to produce G1 (MCS)SvNa (A), which is then subjected to Kpn I digestion followed by fusion of the Kpn I fragment (C) with the linearized pRV109 vector (B). The resulting pREX II retroviral expression vector (D) is driven by a hybrid CMV/MSV/MLV promoter at the 5' LTR and a standard MLV LTR at the 3' end. The 0.44 kb cDNA encoding human granulocyte macrophage colony stimulating factor (GM-CSF), was cloned into the unique Not 1 (5,) and Xho 1 (3,) cloning sites of the pREX II vector (E).

Figure 2:
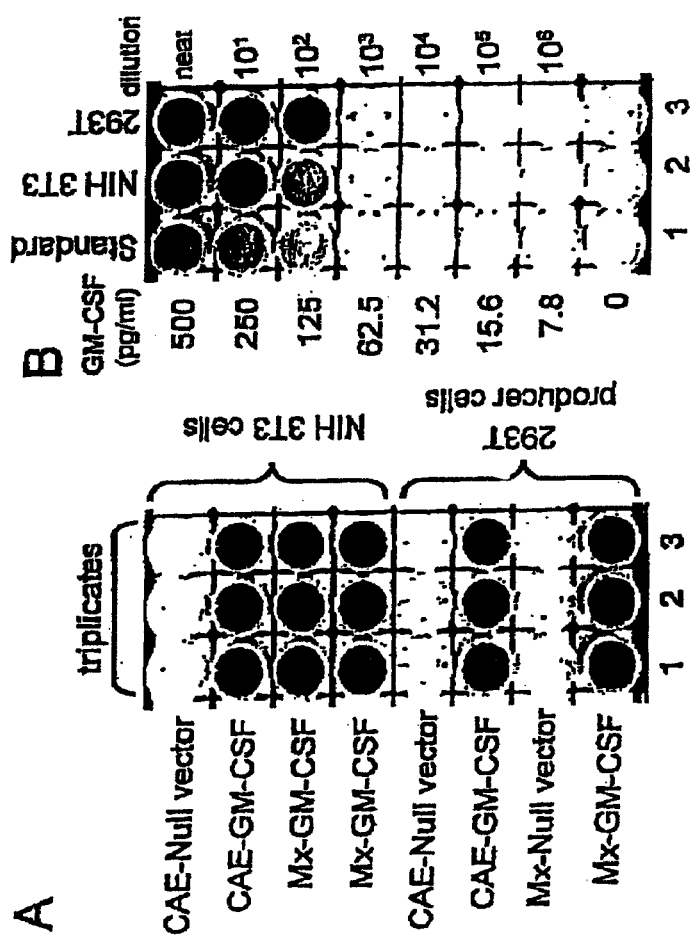

FIG. 2 shows the immunologic detection of human GM-CSF protein secreted by transduced NIH3T3 cells and transfected 293T cells. (A) The darkened ELISA wells indicate immunoreactive human GM-CSF secreted by transduced NIH3T3 and transfected 293T cells, as detected by a polyclonal goat anti-human GM-CSF IgG (R&D Systems, Inc.). (B) Serial dilutions of supernatant collected from transduced NIH3T3 and transfected 293T cell cultures were used to measure immunoreactive human GM-CSF protein (shown as decreasing immunoreactivity with each dilution), against a purified rhGM-CSF standard.

Figure 3:
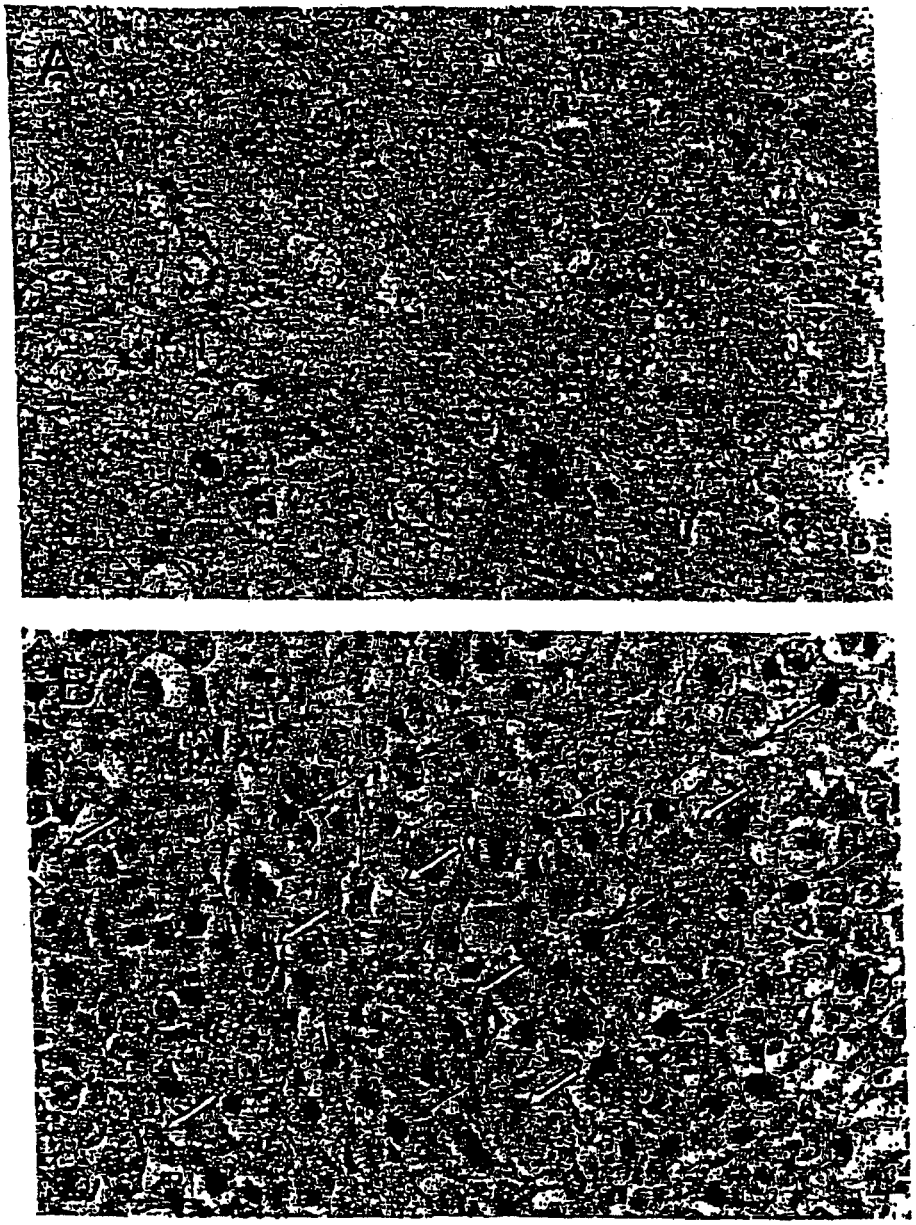

FIG. 3 shows high level transduction of the tumor nodule by intravenous injection of the matrix-targeted retroviral vector bearing a nuclear targeted β-galactosidase gene. (A: X 400) A negative staining control tumor nodule from Mx-null vector-treated animal. (B: X400) A tumor nodule from a Mx-nBg vector-treated animal. β-galactosidase expressing tumor cells (closed arrows) and tumor endothelial cells (open arrows) are shown as reddish-brown nuclear stained cells, counterstained with methyl green.

Figure 4:
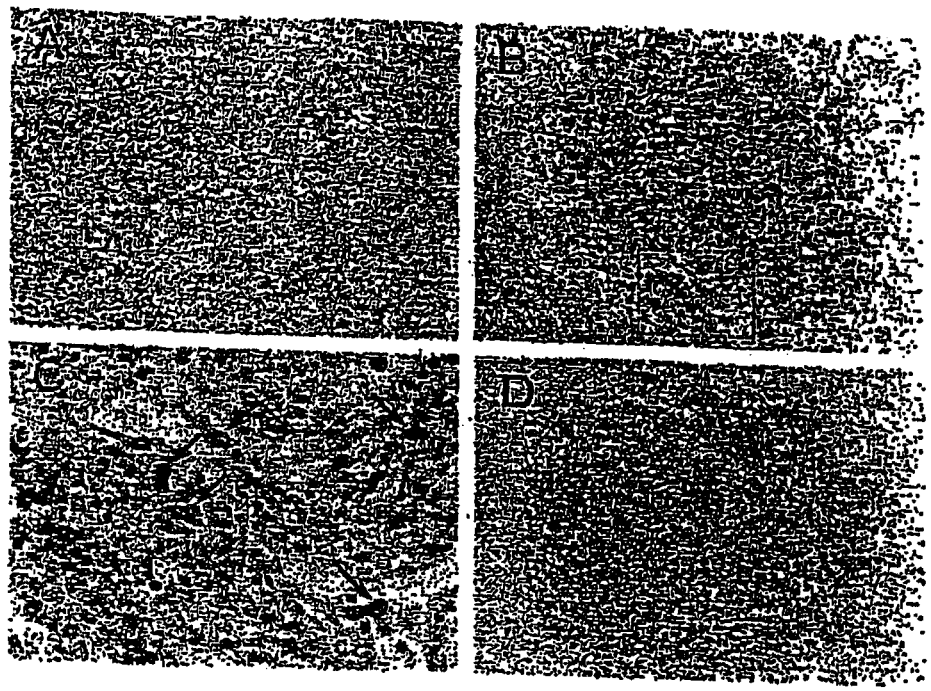

FIG. 4 is a histologic section of a tumor nodule expressing immunoreactive human GM-CSF from nude mice treated with intravenous injections of the matrix-targeted GM-CSF retroviral vector. (A: X 40) A negative staining control tumor nodule from Mx-null vector-treated mouse. (B: X40) A tumor nodule from a Mx-Gm-CSF vector-treated animal. Human GM-CSF expressing tumor cells are shown as reddish-brown nuclear stained cells, counterstained with methyl green. (C: X200) Boxed area in B with human GM-CSF expressing tumor cells are indicated by arrows. (D: X40) Tumor nodule in B as negative control with no primary antibody.

Figure 5:
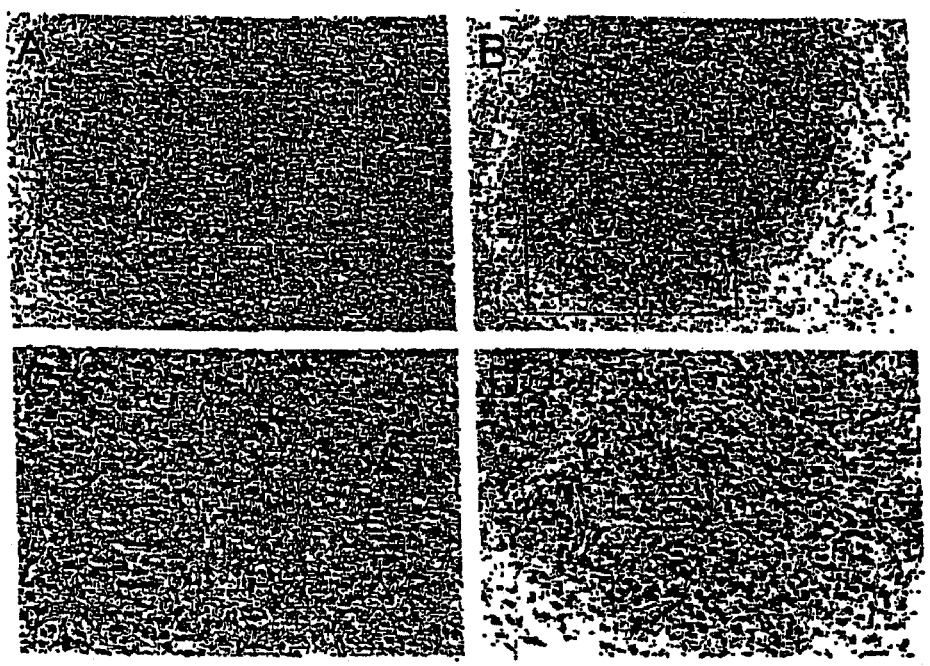

FIG. 5 shows extensive infiltration of the tumor nodule by host mononuclear cells (tumor infiltrating lymphocytes) in mice treated with intravenous injections of the matrix-targeted GM-CSF retroviral vector. (A: 40X) H&E stained tissue section of tumor nodule from a Mx-null vector-treated mouse. (B: X40) H&E stained tissue section of tumor nodule from a Mx-GM-CSF vector-treated animal. (C: X100) Higher magnification of A (boxed area) showing a pleomorphic population of tumor cells, tumor stromal and endothelial cells with minimal mononuclear cell infiltration. (D: X100) Higher magnification of B showing extensive infiltration of host mononuclear cells.

6. DETAILED DESCRIPTION

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

DEFINITIONS

The practice of the present invention will employ, unless otherwise indicated, conventional techniques of immunology, molecular biology, microbiology, cell biology and recombinant DNA. These methods are described in the following publications. See, e.g., Sambrook, et al. MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.); "PCR: A PRACTICAL APPROACH" (M. MacPherson, et al., IRL Press at Oxford University Press (1991)); PCR 2: A PRACTICAL APPROACH (M. J. MacPherson, B. D. Hames and G. R. Taylor eds. (1995)); ANTIBODIES, A LABORATORY MANUAL (Harlow and Lane, eds. (1988)); and ANIMAL CELL CULTURE (R. I. Freshney, ed. (1987)).

As used in the specification and claims, the singular form "a", "an" and "the" include plural references unless the context clearly dictates otherwise. For example, the term "a rtargeted retroviral particle" includes a plurality of particles, including mixtures thereof.

The term "cancer" includes a myriad of diseases generally characterized by inappropriate cellular proliferation, abnormal or excessive cellular proliferation. Examples of cancer include but are not limited to, breast cancer, colon cancer, prostate cancer, pancreatic cancer, melanoma, lung cancer, ovarian cancer, kidney cancer, brain cancer, or sarcomas. Such cancers may be caused by, chromosomal abnormalities, degenerative growth and developmental disorders, mitogenic agents, ultraviolet radiation (UV), viral infections, inappropriate tissue expression of a gene, alterations in expression of a gene, or carcinogenic agents.

The term "treatment" includes, but is not limited to, inhibition or reduction of proliferation of cancer cells, destruction of cancer cells, prevention of proliferation of cancer cells or prevention of initiation of malignant cells or arrest or reversal of the progression of transformed premalignant cells to malignant disease or amelerition of the disease.

The term "subject" refers to any animal, preferably a mammal such as a human. vetinary uses are also intended to be encompassed by this invention.

The present invention provides, in general, compositions and methods for use in cancer immunotherapy. More particularly, this invention is directed to targeted injectable vectors, such as targeted retroviral particles, for use in cancer immunotherapy wherein the targeted retroviral particle comprises a modified viral surface protein for targeting the vector particle and is capable of expressing a cytokine gene. These compositions and methods are based on an observation by the inventors that a targeted retroviral particles expressing a cytokine gene can be administered systemically and achieve (i) high level efficiency of cytokine gene delivery into solid tumors, (ii) secretion of GM-CSF by tumor cells within the solid tumor, and (iii) recruitment of host mononuclear cells (tumor infiltrating lymphocytes, TIL) into the GM-CSF secreting tumor nodules for eradication of primary, metastatic, inaccessible or minimal residual disease.

In one embodiment the invention provides a targeted injectable vector in the form of a targeted retroviral particle comprising a cytokine gene. The retroviral particle is targeted to cancer cells or tumors by modifying the viral surface protein to express a targeting polypeptide. Preferably, the targeting polypeptide recognizes motifs associated with cancer or tumor growth. Examples of motifs for recognition by the targeting polypeptide include, but are not limited to, extra cellular matrix (ECM) or tumor vasculature (see e.g., WO/01/07059 and WO/01/31036, hereby incorporated by reference). By way of example, the targeting polypeptide could recognize the extra cellular matrix (ECM), endothelial cells or stromal cells exposed during tumor growth, angiogenesis or metastasis. Examples of collagen binding motifs that may be used to target the ECM include, but are not limited to, the collagen binding motif derived from the von Willebrand coagulation factor (Takigi, J., et al (1992) *Biochemistry* 32:8530 and WO/01/07059).

The targeted retroviral particle can be generated by conventional methods. By way of example, a three plasmid co-transfection system may be used to construct the retroviral particle. Generally, in such a system, one plasmid comprises the gag-pol genes, a second plasmid comprises the chimeric or hybrid surface proteins for targeting the retroviral particle, and the third plasmid comprises an expression vector containing the cytokine gene (e.g., Examples 1 and 2; Miller (1990) *Human Gene Therapy Vol.* 1, U.S. Pat. No. 5,952,225; Soneoka et al (1995) *Nucl. Acid Research* 23:628; WO/01/07059 and WO/01/31036, hereby incorporated by reference).

Expression vectors suitable for use in expressing the cytokine gene may comprise at least one expression control element operably linked to the nucleic acid sequence encoding the cytokine gene. Expression control elements may be inserted in the vector to control and regulate the expression of the cytokine nucleic acid sequence. Examples of expression control elements include, but are not limited to, lac system, operator and promoter regions of phase λ, yeast promoters, and promoters derived from polyoma, adenovirus, retroviruses, or SV40. The vector may further comprise additional operational elements including, but not limited to, leader sequences, termination codons, polyadenylation signals, and any other sequences necessary or preferred for the appropriate transcription and/or translation of the cytokine nucleic acid sequence. It will be understood by one skilled in the art that the correct combination of required or preferred expression control elements will depend on the gene to be expressed, target tissue and the like. It will be further understood by one skilled in the art that such vectors are constructed using conventional methodology (See e.g. Sambrook et al., (eds.) (1989) "Molecular Cloning, A laboratory Manual" Cold Spring Harbor Press, Plainview, N.Y.; Ausubel et al., (eds.) (1987) "Current Protocols in Molecular Biology" John Wiley and Sons, New York, N.Y.; WO/01/31036, hereby incorporated by reference) or are commercially available.

In a preferred embodiment, the targeted retroviral particles are viral vectors. Examples of viral expression vectors that may be used include, but are not limited to, retroviral vectors, such as lentivirus, vaccinia virus vectors, adenovirus vectors, herpes virus vector, or fowl pox virus vector. In a preferred embodiment, the cytokine gene is incorporated into a retroviral expression vector and packaged into the retroviral particle (see e.g., WO/01/07059 and WO/01/31036, hereby incorporated by reference).

Cytokines modulate the immune system. The cytokine gene incorporated into the expression vector may be any cytokine gene, preferably a cytokine which enhances or stimulates the humoral or cellular immune response. The polynucleotide encoding the gene may be DNA or RNA. The targeted retroviral vector may comprise a polynucleotide encoding the entire cytokine protein or a polynucleotide encoding a portion of the protein necessary for the biological activity of the cytokine. Cytokines include but are not limited to, interleukins, lymphokines, monokines, interferons, colony stimulating factors and chemokines. Examples of specific cytokine that may be used include, but are not limited to, IL-1, TNF, IL-2, IFN-γ, IL-4, IL-7 and GM-CSF. Preferred cytokines are GM-CSF and IL-2. The targeted retroviral vectors may comprise all or part of one or more cytokine genes.

In another embodiment this invention also provides a targeted retroviral particle comprising a modified viral surface protein for targeting the vector (e.g., targeting an extracellular matrix component or tumor vasculature) and a cytocidal gene (e.g., tumor suppressor genes). These targeted retroviral particles may be generated as described herein above, (see, e.g., WO/01/64870) The cytocidal gene may be any gene which inhibits, destroys or prevents cancer cell growth or induces apoptosis in cancer cells. Examples of cytocidal genes includes, but is not limited to, tumor suppressor genes (e.g., p53, RB), thymidine kinases (e.g., HSV thymidine kinase, CMV thymidine kinase) or mutated cyclin G1 genes. The vector may comprise a polynucleotide encoding for an entire cytocidal gene or a portion of a polynucleotide encoding a portion of the cytocidal protein sufficient to exert its biological activity. By way of example, the cytocidal gene may be a dominant negative mutation of the cyclin G1 protein (e.g., WO/01/64870). The targeted retroviral particle comprising a modified viral surface protein for targeting the vector and a cytocidal gene may be used alone or in conjunction with the targeted retroviral particle comprising a modified viral surface protein for targeting the vector and a cytokine gene. Alternatively, both the cytokine and cytocidal gene may be contained within the same targeted retroviral vector.

In an alternative embodiment, the targeted injectable vector may be in the form of nonviral vectors, such as cationic liposomes expressing a cytokine gene or cytocidal gene.

Another embodiment of this invention relates to methods of treating cancer with immunotherapy by administering the targeted retroviral particles described herein to a subject. The term treatment as used herein is intended to include, but is not limited to, administration of the targeted retroviral particles prior to any evidence of disease (e.g., subjects at risk of occurrence of the disease or at risk of recurrence) or to mediate regression of the disease in a subject. The quantity of targeted viral particle comprising a cytokine gene to be administered is based on the titer of virus particles. By way of example, a range of particles to be administered is about $10^9$ to about $10^{12}$ colony forming units (cfu). After administration, the efficacy of the treatment can be assessed by cytokine production by transduced tumors, recruitment into the tumor site of immune cells (e.g., TIL) or antibodies that recognize the tumor antigen, and/or by tumor regression. One skilled in the art would know the conventional methods to assess the aforementioned parameters.

The targeted retroviral particle comprising the cytokine gene may be administered alone or in conjunction with other therapeutic treatments or active agents. For example, the targeted retroviral particle comprising a cytokine gene may be administered with the targeted retroviral particle comprising a cytocidal gene. The quantity of the targeted retroviral particle comprising a cytocidal gene to be administered is based on the titer of the virus particles as described herein above. By way of example, if the targeted retroviral particle comprising a cytokine gene is administered in conjunction with a targeted retroviral particle comprising a cytocidal gene the titer of the retroviral particle for each vector may be lower than if each vector is used alone. The targeted retroviral particle comprising the cytokine gene may be administered concurrently or separately from the targeted retroviral particle comprising the cytocidal gene.

The methods of the subject invention also relate to methods of treating cancer by administering a targeted retroviral particle (e.g., the targeted retroviral vector expressing a cytokine either alone or in conjunction with the targeted retroviral vector expressing a cytocidal gene) with one or more other active agents. Examples of other active agents that may be used include, but are not limited to, chemotherapeutic agents, anti-inflammatory agents, protease inhibitors, such as HIV protease inhibitors, nucleoside analogs, such as AZT. The one or more active agents may be administered concurrently or separately (e.g., before administration of the targeted retroviral particle or after administration of the targeted retroviral particle) with the one or more active agents. One of skill in the art will appreciate that the targeted retroviral particle may be administered either by the same route as the one or more agents (e.g., the targeted retroviral vector and the agent are both administered intravenously) or by different routes (e.g., the targeted retroviral vector is administered intravenously and the one or more agents are administered orally).

An effective amount or therapeutically effective of the targeted retroviral particles to be administered to a subject in need of treatment may be determined in a variety of ways. By way of example, the amount may be based on viral titer or efficacy in an animal model. Alternatively the dosing regimes used in clinical trials may be used as general guidelines. The daily dose may be administered in a single dose or in portions at various hours of the day. Initially, a higher dosage may be required and may be reduced over time when the optimal initial response is obtained. By way of example, treatment may be continuous for days, weeks, or years, or may be at intervals with intervening rest periods. The dosage may be modified in accordance with other treatments the individual may be receiving. However, the method of treatment is in no way limited to a particular concentration or range of the targeted retroviral particle and may be varied for each individual being treated and for each derivative used.

One of skill in the art will appreciate that individualization of dosage may be required to achieve the maximum effect for a given individual. It is further understood by one skilled in the art that the dosage administered to a individual being treated may vary depending on the individuals age, severity or stage of the disease and response to the course of treatment. One skilled in the art will know the clinical parameters to evaluate to determine proper dosage for the individual being treated by the methods described herein. Clinical parameters that may be assessed for determining dosage include, but are not limited to, tumor size, alteration in the level of tumor markers used in clinical testing for particular malignancies. Based on such parameters the treating physician will determine the therapeutically effective amount to be used for a given individual. Such therapies may be administered as often as necessary and for the period of time judged necessary by the treating physician.

While it is possible for the targeted retroviral particle to be administered in a pure or substantially pure form, it is preferable to present it as a pharmaceutical composition, formulation or preparation.

Pharmaceutical compositions comprising the targeted retroviral particles to be used in the methods described herein may be formulated and administered by methods well known in the art (*Remington's Pharmaceutical Sciences*, 20th Edition, Lippincott, William & Wilkins Baltimore, Md.). For example, the compositions of the present invention may comprise an effective amount of the targeted retroviral particles and a pharmaceutically and/or physiologically acceptable carrier. The characteristics of the carrier will depend on the route of administration. Such a composition may contain, in addition to the targeted retroviral particles, diluents, filters, salts, buffers, stabilizers, solubilizers and other materials well known in the art.

The compositions of the may be formulated for various routes of administration by methods well known in the art, including, but not limited to parenteral administration, (e.g., for injection via the intravenous, intramuscular, sub-cutaneous, intratumoral or intraperitoneal routes), oral administration or topical administration. In a preferred embodiment, the targeted retroviral particles are administered intravenously or intraarterially. Upon formulation, the compositions are administered in a manner compatible with the dosage formulation. By way of example, the administration may vary from several times a day to less frequent to administrations, such as once a day or every other day for only a few days such as with a rest period of varying lengths, such as a week. Some variation in dosage will necessarily occur depending on the condition of the subject being treated. The person responsible for administration will, in any event, determine the appropriate dose for the individual subject. Veterinary uses are also intended to be encompassed by this invention.

It is a further object of this invention to provide a kit or drug delivery system comprising the compositions for use in the methods described herein. All the essential materials and reagents required for administration of the targeted retroviral particle may be assembled in a kit (e.g., packaging cell construct or cell line, cytokine expression vector). The components of the kit may be provided in a variety of formulations as described above. The one or more targeted retroviral particle may be formulated with one or more agents (e.g., a chemotherapeutic agent) into a single pharmaceutically acceptable composition or separate pharmaceutically acceptable compositions.

The components of these kits or drug delivery systems may also be provided in dried or lyophilized forms. When reagents or components are provided as a dried form, reconstitution generally is by the addition of a suitable solvent, which may also be provided in another container means. The kits of the invention may also comprise instructions regarding the dosage and or administration information for the targeted retroviral particle. The kits or drug delivery systems of the present invention also will typically include a means for containing the vials in close confinement for commercial sale such as, e.g., injection or blow-molded plastic containers into which the desired vials are retained. Irrespective of the number or type of containers, the kits may also comprise, or be packaged with, an instrument for assisting with the injection/administration or placement of the ultimate complex composition within the body of a subject. Such an instrument may be an applicator, inhalant, syringe, pipette, forceps, measured spoon, eye dropper or any such medically approved delivery vehicle.

The following examples illustrate various aspects of the invention, but in no way are intended to limit the scope thereof.

7. EXAMPLES

Example 1

Construction of the GM-CSF Retroviral Expression Vector

The retroviral expression vector (pREX 11) was created by engineering a multiple cloning site (MSC) into the G1 XSvNa vector (Genetic Therapy, Inc.) to produce G1 (MCS)SvNa (FIG. 1A), which is then subjected to Kpn I digestion followed by fusion of the Kpn I fragment (FIG. 1C) with the linearized pRV109 vector (FIG. 1B). The resulting pREX II retroviral expression vector (FIG. 1D) is driven by a hybrid CMV/MSV/MLV promoter at the 5' LTR and a standard MLV LTR at the 3' end. Bearing the strong CMV promoter and an SV40 ori, this plasmid is suitable for high titer vector production in 293T cells prepared by transient transfection protocols. (Soneoka et al., 1995). The 0.44 kb cDNA encoding human granulocyte macrophage colony stimulating factor (GM-CSF), GenBank accession number NM 000758, flanked by PCR-derived restriction sites was cloned into the unique Not 1 (5') and Xho 1 (3') cloning sites of the pREX II vector (E).

Example 2

Production of Matrix-Targeted Retroviral Vectors Bearing a Human GM-CSF Construct High titer vectors were generated utilizing a transient three plasmid co-transfection system (Soneoka et al., 1995) in which the packaging components gag-pol, a chimeric MLV-based env bearing a von Willebrand factor-derived collagen-binding (matrix-targeting) motif expressed from the CMV promoter, and a retroviral vector bearing were placed on separate plasmids, each containing the SV40 origin of replication. The resulting vectors are referred to as Mx-GM-CSF, CAE-GM-CSF, Mx null, and Mx-nBg to indicate the envelope and gene encoded in each vector. Mx-GM-CSF is a matrix (i.e. collagen)-targeted vector bearing a human GM-CSF construct. CAE-GM-CSF, is a non-targeted vector bearing the wild type MLV 4070A env protein (Morgan et al., 1993). Mx-null is a matrix-targeted vector bearing only the neo gene, and Mx-nBg, is a collagen-matrix-targeted vector bearing a nuclear targeted β-galactosidase gene. The collagen-matrix-targeting results from the insertion of a collagen-binding peptide derived from human von Willebrand factor into the MLV 4070A env protein (Hall et al., 2000). Viral titers in murine NIH3T3 cells were determined as previously described, based on expression of the β galactosidase or neomycin phosphotransferase resistance, neo gene (Skotzko et al., 1995). Viral titer was expressed as number of nuclear β-galactosidase expressing colonies or G418 resistant colony forming units (cfu)/ml, and ranged from 0.3-1.8× $10^7$ cfu/ml.

Example 3

GM-CSF Production in Transduced NIH3T3 and 293T Cell Cultures

To assess the production and secretion of GM-CSF, immunohistochemical staining of transduced cells was conducted using a polyclonal goat antibody raised against a peptide, N1 9, mapping at the amino terminus of human GM-CSF (Santa Cruz Biotechnology, Inc.). GM-CSF production was measured in culture medium collected over 3 days in Mx-GM-CSF transduced NIH3T3 and transfected 293T producer cell cultures using commercially available ELISA kits supplied by R&D Systems, Inc.

Immunoreactive human GM-CSF was noted in 40-50% of transduced NIH3T3 cells and 70-80% of transfected 293T cells (n=4 each group), while GM-CSF production was 32 rig/ml in transduced NIH3T3 cell cultures and 100 ng/ml in transfected 293T cell cultures (FIG. 2).

Example 4

In Vivo Gene Transfer Studies

In vivo gene transfer studies. were conducted in compliance with a protocol approved by the University of Southern California Institution Animal Care and Use Committee. To evaluate the efficiency of targeted gene delivery based on the enforced expression of nuclear β-galactosidase and GM-CSF transgenes in vivo, subcutaneous tumor xenografts were established in 8 week old ~25 gm athymic nu/nu mice by subcutaneous implantation of $1\times10^7$ MiaPaca2 cells. When the tumors have reached a size of ~20 mm³, 200 µl of either Mx-nBg marker vector, Mx-GM-CSF vector, a non-targeted CAE-GM-CSF vector, Mx-null or phosphate buffered saline (PBS, pH 7.4), was injected directly into the tail vein daily for 10 days (cumulative vector dose: $2\times10^7$ cfu for each vector). The mice were sacrificed by cervical dislocation one day after completion of one treatment cycle.

Histologic Examination of Harvested Tumor Nodules and Immunohistochemical Analysis for the Presence of β-Galactosidase Transgene (Gordon et al., 2000b).

Harvested tumor nodules were either quick frozen in liquid nitrogen or fixed in 10% formalin. Formalin-fixed tissue sections were stained with hematoxylin-eosin. Transduction efficiency was determined by immunohistochemical staining of the tumor nodules, using a mouse monoclonal antibody directed against the β-galactosidase antigen (GAL-40, Sigma, St. Louis Mo., USA) followed by analysis using an Optimas imaging system (Optimas Corporation, Bothell, Wash., USA). Transduction efficiency (expressed as %) is determined by counting the number of β-galactosidase positive cells in three high power fields per tumor nodule, divided by the total number of cells×100.

Immunostaining for GM-CSF Protein in Tumor Tissues (Miller et al., 2000).

For detection of the human GM-CSF protein in harvested tumors, tumor tissues harvested at the end of the experiment were frozen immediately in liquid nitrogen and kept at −70° C. until used. Five µm tissue sections were cut and fixed in ice-cold acetone for 10 min. A goat polyclonal anti-GM-CSF monoclonal antibody was supplied by Santa Cruz Biotechnology, Inc. The slides were blocked with 2% normal goat serum for 10 min, washed in phophate-buffered saline, and the primary antibody to GM-CSF diluted at 1:50 was added on the slides for 60 min. Then, the slides were washed three times with PBS and a secondary antibody, anti-goat IgG conjugated with peroxidase (1:100: Vector Laboratories, Burlingame Calif., USA) was added to the slides for 30 min. The slides were washed five times with PBS and developed with a DAB substrate kit (Vector Laboratories). After counterstain with methyl green, the slides were examined for presence of brownish-red immunostaining material indicating presence of the GM-CSF transgene in tumor tissues. The efficiency of gene delivery (expressed as %) is determined by counting the number of immunoreactive cells to the anti-GM-CSF antibody in three high power fields per tumor nodule, divided by the total number of cells×100.

Immunoreactive β-galactosidase was noted in ~35% of cells throughout the tumor nodules of Mx-nBg vector-treated animals (FIG. 3B), while no immunoreactive protein was noted in the control Mx-null vector-treated tumors (FIG. 3A). Consistent with the high level transduction of tumor nodules noted previously with the Mx-nBg vector, immunreactive human GM-CSF protein was noted in ~35% of cells throughout the tumor nodules of Mx-GM-CSF vector-treated mice (FIG. 4B-C) compared to <1% in CAE-GM-CSF vector-treated and Mx-null vector-treated mice (FIG. 4A).

Example 5

Recruitment of Host Mononuclear Cells into the Tumor Nodules of Mice Treated with the Mx-GM-CSF Retroviral Vector Extensive infiltration of host mononuclear cells was noted in tumor nodules of Mx-GM-CSF-treated mice (FIGS. 5B&D) compared to minimal mononuclear infiltration in CAE-GM-CSF, Mx-null vector- and PBS-treated animals (FIGS. 5A&C). Within the tumor nodule, the tumor infiltrating lymphocyte (TIL) to tumor cell (T) ratio was 1:20 in Mx-GM-CSF-treated mice compared to 1:90 in nontargeted CAE-GM-CSF vector-treated mice, and 1:99 in Mx-null and PBS-treated animals. These findings indicate successful recruitment of host mononuclear cells into the tumor nodule by GM-CSF secreting cells in Mx-GM-CSF vector-treated mice.

Example 6

Bimodal Therapy In Vivo Efficacy Studies

To evaluate bimodal therapy a matrix a targeted retroviral vector carrying a cytocidal gene, specifically a dominant negative mutant cyclin G1 gene was constructed using the methods described herein above. The resulting vector is desiganted Mx-dnG1. These studies were conducted in immune competent Balb/c mice (weighing ~25 gms), in compliance with a protocol approved by the University of Southern California Institution Animal Care and Use Committee.

To evaluate the efficacy of single versus dual gene therapy in vivo, subcutaneous tumors were established in immune competent Balb/c mice by subcutaneous implantation of $1 \times 10^6$ murine colon-26 cancer cells (NCI, Bethesda Md., USA). Three days later, 200 ml of either the Mx-dnG1 vector (cumulative dose: $1.7 \times 10^8$ cfu/mouse), Mx-GM-CSF vector (cumulative dose: $1.7 \times 10^8$ cfu/mouse), a combination of Mx-dnG1 and Mx-GM-CSF vectors (cumulative dose of each vector: $8 \times 10^7$ cfu/ml) or an equivalent volume of phosphate buffered saline (PBS, pH 7.4) placebo control was injected intravenously twice a day for 5 days. The size of the tumor was measured every 4 days with a Vernier caliper, using the formula for calculating the volume of ellipsoid objects: Tumor Volume, $mm^3 = \frac{4}{3} p\ r_1\ r_2\ r_3$. At the end of 5 days, the tumors were resected, and the animals were given a tumor re-challenge one week after completion of vector treatment. The significance of differences in mean tumor volumes among the four treatment groups were evaluated using ANOVA.

To evaluate a dose-dependent response to the Mx-GM-CSF vector in vivo, $5 \times 10^6$ cells were implanted subcutaneously, and when the tumors reached a size of ~35-40 $mm^3$, 200 ml of either a low-dose (cumulative dose: $8 \times 10^7$ cfu/mouse) or high-dose Mx-GM-CSF vector (cumulative dose: $1.7 \times 10^8$ cfu/mouse), or an equivalent volume of phosphate buffered saline (PBS, pH 7.4) placebo control was injected directly into the tail vein each day for 16 days. The mice were sacrificed by cervical dislocation one day after completion of treatment. The significance of differences in tumor volumes among the three treatment groups was evaluated using ANOVA.

The combination of the vectors Mx-GM-CSF and Mx-dnG1 induced the greatest inhibition of tumor growth ($p<0.05$), and to a lesser extent the MX-dnG1 or Mx-GM-CSF alone. Notably, only half the dose of each vector was given to attain the desired anti-tumor effect.

The combination of immunotherapy with radical surgery, chemotherapy and/or radiation therapy has the potential of eradicating minimal residual disease. In the United States, over 150 approved Phase 1/11 gene therapy protocols involve the use of genetically to engineered syngeneic or allogeneic cells (tumor cells, T cells, dendritic cells and fibroblasts) for vaccine therapy. Cytokine genes used for immunotherapy include IL-1, TNF, IL-2, IFN-y, IL-4, IL-7 and GM-CSF (Foreman et al., 1993; Fearon et al., 1990; Blankenstein et al., 1991; Asher et al., 1991; Tepper et al., 1994; Dranoff et al., 1993; Knobloch et al, 1991; Gansbacher et al., 1991). Other immunostimulatory molecules such as the T-cell co-stimulatory molecule B7.1 (Guinan et al., 1994) or a foreign MHC molecule (Nabel et al., 1993) have also been used to generate anti-tumor immunity.

The major goal of the use of immunostimulatory cytokines is the activation of tumor-specific T lymphocytes capable of rejecting tumor cells from patients with low tumor burden or to protect patients from recurrence of the disease. Treatment of rodents with cancer xenografts with this strategy have resulted in regression of pre-existing tumors and cure of the animals from their disease. Further, some animals have retained immunological memory and resisted a second challenge with the parental tumor cells (Gilboa, 1996; Mackensen et al., 1997).

The mechanisms by which transduced cytokines enhance tumor immunity are the subject of much investigation. Without being bound by theory, they may act by increasing the recruitment of cytotoxic T cells able to recognize tumor-specific antigens (e.g. IL-4) (Golumbek et al., 1991) or of CD4-positive cells (e.g. TNF and IL-7) (Asher et al., 1991; Hock et al., 1991), or they may increase tumor antigen expression by upregulating MHC Class I antigens (e.g. IFN-$\gamma$) (Watanabe et al., 1989), thereby rendering non-transduced target cells more vulnerable to cytotoxic attack. Alternatively, a combination of these effects may be produced. For example, IL-2 can recruit both cytotoxic T and NK cells directly and can also induce release of the secondary cytokine IFN-$\gamma$ (Main et al., 1985), which augments MHC expression on tumor cells (Coze et al., 1995; Ucar et al., 1995; Handgretinger R et al., 1989). Additional (non-lymphocytic) effector mechanisms appear to contribute as well, since the tumor site is often infiltrated with eosinophils and macrophages. As a final mechanism, some cytokines such as GM-CSF may enhance the activity and differentiation of antigen presenting cells, which ingest tumor cells and present their antigens either in association with Class I or Class II MHC molecules, thereby recruiting CD8+ or CD4+ tumor specific T lymphocytes (Dranoff et al., 1993).

The inhibition of subcutaneous tumor growth in nude mice by intravenous administration of a matrix-targeted retroviral vector bearing a cytocidal/cytostatic cyclin G1 construct (Gordon et al., 2000a) was recently reported. These retroviral vectors displayed a collagen-binding motif derived from von Willebrand coagulation factor that could target extracellular matrix (ECM) exposed during tumor growth, angiogenesis, and metastasis. Enhanced vector penetration and transduction of tumor nodules was demonstrated and correlated with therapeutic efficacy without associated toxicity. In the present study, we demonstrated high level GM-CSF secretion in NIH3T3 and 293T cell cultures transduced or transfected, respectively, with a matrix-targeted retroviral vector bearing a human GM-CSF construct, as well as high level transduction of subcutaneous human cancer xenografts in nude mice by repeated intravenous injections of the Mx-GM-CSF vector. Further, the enforced expression and secretion of GM-CSF by transduced cells throughout the tumor nodule resulted in recruitment of host mononuclear cells into the tumor nodule. These studies were conducted in athymic nude mice lacking cytotoxic T cells. In immune competent mice with a complete repertoire of T lymphocytes and antigen-presenting B cells, dendritic cells and macrophages, regression of the tumor nodules and establishment of long term antitumor immunity would be expected to occur, particularly when tumor antigens are presented simultaneously by concomitant administration of a matrix-targeted vector bearing a cytocidal gene.

The data demonstrates that a targeted retroviral vector comprising a cytokine gene, such as a matrix (i.e. collagen)-targeted retroviral vector bearing a human GM-CSF construct can be injected intravenously to achieve (i) high level efficiency of cytokine gene delivery into solid tumors, (ii) secretion of GM-CSF by tumor cells within the solid tumor, and (iii) recruitment of host mononuclear cells (tumor infiltrating lymphocytes, TIL) into the GMCSF secreting tumor nodules for eradication of primary, metastatic, inaccessible or minimal residual disease.

It is to be understood that while the invention has been described in conjunction with the above embodiments, that the foregoing description and the following examples are intended to illustrate and not limit the scope of the invention. Other aspects, advantages and modifications within the scope of the invention will be apparent to those skilled in the art to which the invention pertains.

REFERENCES

Asher A L, Mule J J, Kasid A, Restifo N P, Salo J C, Reichert C M, Jaffe G, Fendly B, Kriegler M, Rosenberg Sa. Murine tumor cells transduced with the gene for tumor necrosis factor-alpha. Evidence for paracrine immune effects of tumor necrosis factor against tumors. J Immunol 146:3227-3234, 1991.

Blankenstein T, Zin Z H, Uberla K, Muller W, Rosen H, Volk H I D. Diamantstein T. Tumor suppression after tumor cell-targeted tumor necrosis factor alpha transfer. J Exp Med 173:1047-1052, 1991.

Borrello 1, Sotomayor E M, Cooke S, Levitsky H I. A universal granulocyte-macrophage colony stimulating factor-producing bystander cell line for use in the formulation of autologous tumor cell-based vaccines. Hum Gene Ther 10:1983-1991, 1999.

Coze C, Aalto-Setala K, Brenner M, Chiang Y, Gangavalli R, Leimig T. Characteristics and immunomodulatory properties of human neuroblastoma cells after retroviru-mediated gene transfer of the cytokine genes IL-2 and IFN-gamma. Transgenics 1:585-595, 1995.

Dranoff G, Jaffee E, Lazenby A, Golumbek P, Levitsky H, Brose K, Jackson V, Hamada H, Pardoll D, Mulligan R. Vaccination with irradiated tumor cells engineered to secrete murine granulocyte-macrophage colony-stimulating factor stimulates potent specific, and long-lasting antitumor immunity. Proc Natl Acad Sci USA 90:3539, 1993.

Fearon E R, Pardoll D M, Itaya T, Golumbed P, Levitsdy H I, Simons J W, Karasuyama H, Vogelstein B, Frost P (1990) Interleukin-2 production by tumor cells bypasses Thelper function in the generation of an antitumor response. Cell 60, 397-403.

Fong T C, Sauter S L, Ibanez C E, Sheridan P L, Jolly D J. The use and development of retroviral vectors to deliver cytokine genes for cancer therapy. Crit Rev Therap Drug Carrier Systems 17:1-60, 2000.

Foreman N K, Rill D R, Coustan-Smith E, Douglass E C, Brenner M K. Meachanisms of selective killing of neuroblastoma cells by natural killer cells and lymphokine activated killer. Potential for residual disease eradication. Br. J. Cancer 67:933-938, 1993.

Gansbacher B, Gee C, Houghton A N, et al., Retroviral lymphokine gene transfer induced secretion of interleukin-2 (IL-2) or interferon-gamma (IFN-gamma) by human melanoma cells. Proc Arum Meet Am Assoc Cancer Res 32:A1 514, 1991 (Abstract).

Gilboa E (1996) Immunotherapy of cancer with genetically modified tumore vaccines. Semin Oncol 23, 101-107.

Golumbek P T, Lazenby A J, Levitsky H I, Jaffee L M, Karasuyama H, Baker M, Pardoll D M. Treatment of established renal cancer by tumor cells engineered to secrete interleukin-4. Science 254:713-716, 1991.

Gordon E M, Liu P X, Chen Z H, Liu L, Whitley M D, Gee C, Groshen S, Hinton D R, Beart R W, Hall F L. Inhibition of metastatic tumor growth in nude mice by portal vein infusions of matrixtargeted retroviral vectors bearing a cytocidal cyclin G1 construct. Cancer Res. 60:3343-3347, 2000a.

Gordon E M, Liu P X, Chen Z H, Liu L, Whitley M, Liu L, Wei D, Groshen S, Hinton D R, Anderson W F, Beart R W, Hall F L. Systemic administration of a matrix-targeted retroviral vector is efficacious for cancer gene therapy in mice. Hum Gene Ther, 2000b, in press.

Guinan E C, Gribben, J G, Boussiotis V a, Freeman G J, Nadler L M. Pivotal role of the B7:CD28 pathway in transplantation tolerance and tumor immunity. Blood 84:3261-3282, 1994.

Hall F L, Liu L, Zhu N L, Stapfer M, Anderson W F, Beart R W, Gordon, E M. Molecular engineering of matrix-targeted retroviral vectors incorporating a surveillance function inherent in von Willebrand factor. Hum Gene Ther 11:983-993, 2000.

Handgretinger R, Kimmig A, Lang P Daurer B, Kuci S, Bruchelt G, Treuner J, Niethammer D. Interferon-gamma upregulates the susceptibility of human neuroblastoma cells to interleukin-2-activated natural killer cells. Nature Immun Cell Growth Regul 8/4:189-196, 1989.

Hock H, Dorsch M, Diamantstein T, Blankenstein T. Interleukin 7 induces CD4+ T cell dependent tumor rejection. J Exp Med 174:1291-1298, 1991.

Jaffee E M. Immunotherapy for cancer. Ann NY Acad Sci 886:67-72, 1999.

Kim J J, Yang J S, Lee D J, Wilson D M, Nottingham L K, Morrison L, Tsai A, Oh J, Dang K, Dentchev T, Agadjanyan M G, Sin J I, Chalian A A, Weiner D B. Macrophage colony-stimulating factor can modulate immune responses and attract dendritic cells in vivo. Hum Gene Ther 11:305-321, 2000.

Knobloch C, Friedrich W. T cell receptor diversity in severe combined immunodeficiency following HLA-haploidentical bone marrow transplantation. Bone Marrow Transplantation 8:383-387, 1991.

Kurane S, Arca M T, Aruga A, Krinock R A, Krauss J C, Chang A E. Cytokines as an adjuvant to tumor vaccines: efficacy of local methods of delivery. Ann Surg Oncol 4:579-585, 1997.

Liu L, Liu L, Anderson W F, Gordon E M, Hall F L. Incorporation of tumor vasculature targeting motifs (TVTMs) into MLV env escort proteins enhances retroviral binding and transduction of human enclothelial cells. J Virol, 74:5320-5328, 2000.

Mackensen A, Lindemann A, Mertelsmann R (1997) Immunostimulatory cytokines in somatic cells and gene therapy of cancer. Cytokine Growth Factor Rev 8, 119-128.

Main E K, Lampson L A, Hart M K et al. Human neuroblastoma cell lines are susceptible to lysis by natural killer but not cytotoxic T lymphocytes. J Immunol 135:242-246, 1985.

Mellstedt H, Fagerberg J, Frodin J E, Henriksson L, Hjelm-Skoog A L, Liljefors M, Ragnhammar P, Shetye J, Osterborg A. Augmentation of the immune response with granulocyte-macrophage colony-stimulating factor and other hematopoietic growth factors. Curr Opin Hematol 6:169-175, 1999.

Mendiratta S K, Quezada A, Matar M, Thull N M, Bishop J S, Nordstrom J L, Pericle F. Combination of interleukin 12 and interferon a gene therapy induces a synergistic antitumor response against colon and renal cell carcinoma. Hum Gene Ther 11:1851-1862, 2000.

Miller P W, Sharma S, Stolina M, Butterfield L H, Luo J, Lin Y, Dohadwala M, Batra R K, Wu L, Economou J S, Dubinett S M. Intratumoral administration of adenoviral interleukin 7 genemodified dendritic cells augments specific antitumor immunity and achieves tumor eradication. Hum Gene Ther 11:53-65, 2000.

Morgan, R. A., Nussbaum, 0., Muenchau D. D., Shu, L., Couture, L., AND Anderson, W. F. Analysis of the functional and host range-determining regions of the murine ecotropic and amphotropic retrovirus envelope proteins. J. Virol. 67: 4712-4721, 1993.

Nabel G J, Nabel E G, Yang Z Y, Fox B A, Plautz G E, Gao X, Huang L, Shu S, Gordon D, Chang A E. Direct gene transfer with DNA-liposome complexes in melanoma: expression, biologic activity, and lack of toxicity in humans. Proc Natl Acad Sci USA 90:11307-11311, 1993.

Nagai E, Ogawa T, limbo A, Suzuki T. Irradiated tumor cells adenovirally engineered to secrete granulocyte/macrophage-colony-stimulating factor establish antitumor immunity and eliminate pre-existing tumors in syngeneic mice. Cancer Immunol Immunother 47:72-80, 1998.

Skotzko M J, Wu L T, Anderson W F, Gordon E M, Hall F L. Retroviral vector-mediated gene transfer of antisense cyclin G1 (CYCG1) inhibits proliferation of human osteogenic sarcoma cells. Cancer Research 55:5493-5498, 1995.

Soneoka Y, Cannon P M, Ramsdale E E, Griffiths J C, Gaetano R, Kingsman S M, Kingsman A J. A transient three-plasmid expression system for the production of high titer retroviral vectors. Nucleic Acid Res 23:628-633, 1995.

Sub. K W, Piantadosi S, Yazdi H A, Pardoll D M, Brem H, Choti M A. Treatment of liver metastases from colon carcinoma with autologous tumor vaccine expressing granulocyte-macrophage colony-stimulating factor. J Surg Oncol 72:218-224, 1999.

Tepper R I, Mule J J. Experimental and clinical studies of cytokine gene-modified tumor cells. Huron Gene Ther 5:153-164, 1994.

Ucar K, Seeger R C, Challita P M, Watanabe C T, Yen T I L, Morgan J P, Amado R, Chou E, McCallister T, Barber J R et al. Sustained cytokine production and immunophenotypic changes in human neuroblastoma cell lines transduced with a human gamma interferon vector. Cancer Gene Ther 2:171-181, 1995.

Warren T L, Weiner G J. Uses of granulocyte-macrophage colony-stimulating factor in vaccine development. Curr Opin Hematol 7:168-173, 2000.

Watanabe Y, Kuribayashi K, Miyatake S, Nishihara K, Nakayama E, Taniyama T, Sakata T. Exogenous expression of mouse interferon gamma cDNA in mouse neuroblastoma C1 300 cells results in reduced tumorigenicity by augmented anti-tumor immunity. Proc Natl Acad Sci USA 86:9456-9460, 1989.

What is claimed is:

1. A pharmaceutical composition comprising a targeted retroviral vector particle comprising a modified viral surface protein comprising a collagen binding motif obtained from von Willebrand coagulation factor for targeting the vector, and an immunostimulatory cytokine gene, and a second targeted retroviral vector particle comprising a modified viral surface protein comprising a collagen binding motif obtained from von Willebrand coagulation factor for targeting the second vector and a cytocidal gene, wherein the cytocidal gene is thymidine kinase and the immunostimulatory cytokine is GM-CSF, and wherein the titer of the retroviral particle for each vector is lower than if each vector is used alone.

2. The pharmaceutical composition of claim 1, wherein the second targeted retroviral particle is targeting the extracellular matrix or tumor vasculature.

3. A composition comprising a targeted retroviral vector particle comprising a modified viral surface protein comprising a collagen binding motif obtained from von Willebrand coagulation factor for targeting the vector and an immunostimulatory cytokine gene and a targeted retroviral vector particle comprising a modified viral surface protein comprising a collagen binding motif obtained from von Willebrand coagulation factor for targeting the vector and a cytocidal gene, wherein the cytocidal gene is thymidine kinase and the immunostimulatory cytokine is GM-CSF, and wherein the titer of the retroviral particle for each vector is lower than if each vector is used alone.

4. The composition of claim 3, further comprising a pharmaceutical excipient.

5. A method for treating a solid tumor in a subject comprising administering to the subject an effective amount of the pharmaceutical composition of claim 1, wherein administration is intravenous, intratumoral, intraperitoneal, or intraarterial, and wherein said treatment results in a reduction in tumor volume.

6. A method for treating a solid tumor in a subject comprising administering to the subject an effective amount of the pharmaceutical composition of claim 4, wherein administration is intravenous, intratumoral, intraperitoneal, or intraarterial, and wherein said treatment results in a reduction in tumor volume.

* * * * *